T 868,003

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED NOVEMBER 18, 1969

868 O.G. 729

729,834

LIQUID POLYESTER COMPOSITION AND METHOD OF PREPARATION

Hugh J. Hagemeyer, Jr., and Jon Marc Johnson, Longview, Tex., assignors to Eastman Kodak Company, Rochester, N.Y., a corporation of New Jersey

Original application Sept. 23, 1963, Ser. No. 310,924. Divided and this application Feb. 20, 1968. Published Nov. 18, 1969

Int. Cl. C08f *45/38;* C07c *69/44*

U.S. Cl. 260—31.6

No Drawing. 19 Pages Specification

The liquid polyester product of adipic acid, 2,2,4-trimethylpentane-1,3-diol, and a terminating agent selected from the group consisting of (a) a monocarboxylic acid and (b) a monoester of said acid and 2,2,4-trimethylpentane-1,3-diol, is useful as a plasticizer (e.g., for polyvinyl chloride).